United States Patent [19]

Paridon et al.

[11] 4,303,793

[45] Dec. 1, 1981

[54] AQUEOUS CARBAMATE DISPERSIONS

[75] Inventors: Leo J. Paridon, Doylestown; Robert E. Downing, Wadsworth, both of Ohio

[73] Assignee: PPG Industries, Inc., Pittsburgh, Pa.

[21] Appl. No.: 189,278

[22] Filed: Sep. 22, 1980

Related U.S. Application Data

[63] Continuation-in-part of Ser. No. 19,536, Mar. 12, 1979, abandoned, which is a continuation of Ser. No. 788,957, Apr. 19, 1977, abandoned.

[51] Int. Cl.³ .................. C07C 125/04; C07C 125/06
[52] U.S. Cl. ...................... 560/24; 560/30; 560/132
[58] Field of Search .................. 71/DIG. 1, 107, 106; 424/300; 560/24, 30, 132

[56] References Cited

U.S. PATENT DOCUMENTS

| | | | |
|---|---|---|---|
| 2,615,916 | 10/1952 | Allen | 560/24 |
| 2,695,225 | 11/1954 | Witman | 71/111 |
| 2,784,072 | 3/1957 | Garman et al. | 71/111 |
| 2,812,247 | 11/1957 | Gysin et al. | 71/70 |
| 3,024,269 | 3/1962 | Barthel, Jr. et al. | 560/31 |
| 3,391,180 | 7/1968 | Haubein | 560/132 |
| 3,399,228 | 8/1968 | Herrett et al. | 560/163 |
| 3,402,245 | 9/1968 | Lemin et al. | 424/300 |
| 3,404,975 | 10/1968 | Wilson et al. | 71/100 |
| 3,433,826 | 3/1969 | Heiss et al. | 424/300 X |
| 3,546,343 | 12/1970 | Payne, Jr. et al. | 424/300 |
| 3,764,695 | 10/1973 | Chupp | 424/300 |
| 3,791,811 | 2/1974 | French et al. | 71/DIG. 1 |
| 3,938,986 | 2/1976 | Pray | 71/106 X |
| 3,948,636 | 4/1976 | Marks | 71/112 |
| 4,061,770 | 12/1977 | Marks | 71/DIG. 1 |

OTHER PUBLICATIONS

Herbicidal Handbook of the Weed Sciences Society of America, Weed Society of America, 3rd Ed., (1974), pp. 341-346.

*Primary Examiner*—Joseph Paul Brust
*Attorney, Agent, or Firm*—Edward J. Whitfield

[57] ABSTRACT

A stable, flowable aqueous dispersion of agriculturally acceptable carbamate compound is prepared by wetmilling an aqueous carbamate suspension, said suspension prepared by subsurface injection of molten carbamate into a stirred aqueous salt solution.

3 Claims, No Drawings

AQUEOUS CARBAMATE DISPERSIONS

CROSS-REFERENCE TO RELATED APPLICATION

This application is a continuation-in-part of now abandoned application Ser. No. 19,536, filed Mar. 12, 1979, which is a continuation of Ser. No. 788,957, filed Apr. 19, 1977, now abandoned.

FIELD OF THE INVENTION

This invention relates to preparing stable, flowable, aqueous dispersions of one or more agriculturally acceptable carbamate compounds. Aqueous suspensions of agricultural compounds, for example, herbicides, pesticides and other agriculturally useful adjuvants are typically prepared by wet-milling the granular material in the presence of dispersing agents as described, for example, in U.S. Pat. No. 4,061,770.

Carbamate compounds suitable for agricultural purposes, e.g. alkyl N-phenylcarbamates, prepared, as described, for example, in U.S. Pat. No. 2,615,916, are typically recovered from the crude reaction mixture in the molten state which melt is further processed by, for example, flaking to a granular solid.

It has been found that in the preparation of stable, flowable, aqueous dispersions of carbamate compounds that the melt may be used directly without the need to first process the melt to the granular state.

DESCRIPTION OF THE INVENTION

In accordance with this invention, a stable, flowable, aqueous dispersion of one or more agriculturally acceptable carbamate compounds is prepared by injecting molten carbamate into a stirred aqueous salt solution such that the molten carbamate penetrates beneath the surface of the stirred salt solution and forms therein a suspension of carbamate particles at least 80 percent of said particles having a size in the range of 500 to 3500 microns. This aqueous suspension of carbamate particles is then processed using conventional wet-milling and grinding apparatus and techniques to produce a stable dispersion of carbamate particles of the desired size; typically carbamate particle size in the finished dispersion is less than 20 microns and usually in the range of 1 to 10 microns.

The agriculturally acceptable carbamate compounds useful in accordance with this invention are substantially water insoluble, i.e. solubility in water is not more than one percent by weight, have a melting point of from about 40° C. to about 300° C., are stable in the molten state, and have a hardness value permitting wet-milling and grinding to a particle size of less than 20 microns, preferably 1 to 10 microns. Carbamate compounds particularly suited for use in accordance with this invention are the alkyl N-phenylcarbamates and the phenyl N-alkylcarbamates disclosed, for example, in U.S. Pat. No. 3,938,986. Some examples of carbamates particularly preferred for use in accordance with this invention are isopropyl N-phenylcarbamate, isopropyl N-m-chlorophenylcarbamate, 4-chlorophenyl N-methylcarbamate, 4-chlorophenyl N,N-dimethylcarbamate, and 2-chlorophenyl N-n-propylcarbamate.

The aqueous salt solution into which the carbamate is injected is an aqueous solution of alkali or alkaline earth metal salts, some examples of which are sodium chloride, potassium chloride, sodium sulfate, potassium sulfate, sodium nitrate, potassium nitrate, calcium chloride or the like. Sufficient salt is used such that the aqueous salt solution has a specific gravity of from 90 to 110 percent, preferably from 95 to 105 percent of the specific gravity of the molten carbamate or of the heaviest carbamate in the melt if more than one carbamate is used. The temperature of the aqueous salt solution is, of course, maintained at a temperature below the temperature of the molten carbamate and is typically maintained at a temperature of from about 10° C. to about 50° C. below the temperature of the molten carbamate, although the precise temperature is not particularly critical.

The rate of injection of the molten carbamate into the aqueous salt solution and the rate of circulation of the stirred salt solution will of course vary depending upon the relative quantities of carbamate to salt solution, equipment size and the like, all of which parameters may be determined by straightforward empirical testing. The carbamate content of the finished dispersion may vary considerably and may contain from about 10 to about 70 weight percent, usually from 30 to 50 weight percent carbamate.

The compositions of this invention may of course contain conventional additives, such as dispersing agents, emulsifiers and the like, the type and quantity of which will depend on the concentration of the dispersion and the type of carbamate dispersed. Straightforward tests, e.g. centrifugation, are used to determine the suitability of various available dispersing agents.

Although the invention is particularly suited for producing aqueous carbamate dispersions, it is believed equally applicable to producing aqueous dispersions of other agricultural compounds and adjuvants typically used in combination with such carbamates.

The aqueous dispersions produced by the process of this invention are both stable and flowable, i.e. they do not set-up after several months' storage at ambient temperature and are readily amenable for use in typically used agricultural spraying equipment. The flowability and stability of the dispersions of this invention are such that the dispersion remains homogeneous when centrifuged for 4 to 6 minutes at temperatures of 15° to 35° C. at a radius of 5 to 7 inches at a rate of 2000 to 2500 revolutions per minute.

The invention is further illustrated but is not intended to be limited by the following Example.

EXAMPLE

A. Preparation of Carbamate

A 1250 pound batch of isopropyl N-phenylcarbamate was made according to the process described in U.S. Pat. No. 2,615,916 as follows:

Six hundred and seventy (670) pounds of 50 percent aqueous sodium hydroxide solution were added to one hundred and fifty (150) gallons of water contained in a reactor kettle equipped with a stirrer, heating, and cooling means. The temperature was maintained below 60° F., and the solution was continuously stirred. Seven hundred and fifteen (715) pounds of aniline were then added; the temperature was lowered to 50° F. and the pH of the solution was adjusted to between 7.0 and 8.0 and maintained thereat while one thousand and fifty (1050) pounds of isopropylchloroformate were added to form isopropyl N-phenylcarbamate. When 99 to 99.5 percent of the aniline had reacted, the reaction mixture was pumped into a wash kettle and heated with stirring to about 185° to 210° F. until about 95 percent of the isopropyl N-phenylcarbamate had melted. The stirring was stopped, and the mixture was allowed to separate into two phases, the lower of which, i.e., the aqueous salt phase, was drained away. An equal volume of hot water (200° F.) was added to the remaining phase comprised primarily of molten isopropyl N-phenylcarbamate, and the mixture was agitated for 20 minutes, and then allowed to separate into two phases. The upper phase comprising washed molten isopropyl N-phenylcarbamate was pumped into a second wash kettle and washed with 200 gallons of dilute hydrochloric acid solution maintained at 185° F. The washing of the mixture in the second wash kettle was continued, until a 25 milliliter sample of the wash kettle showed that a ½ inch cube of solid isopropyl N-phenylcarbamate heated and mixed with 25 milliliters of distilled water gave no color or only a slight bluish tinge when 3 drops of a solution containing 5 grams of calcium hypochlorite per 100 milliliters of water were added to the mixture of water and isopropyl N-phenylcarbamate after the mixture was cooled to ambient temperature (65° F.).

After the washing with hydrochloric acid solution was completed, the phases were allowed to separate. The upper washed phase of molten isopropyl N-phenylcarbamate (1250 pounds) which was free of aniline was pumped to a holding tank and maintained in the molten state at 190° to 210° F.

B. Preparation of Aqueous Carbamate Dispersion

An aqueous salt solution containing 150 gallons of water, 350 pounds of potassium chloride, 31 pounds of POLYFON T ® (lignin sulfonate), and 6 pounds of SURFYNOL 104 E ® (a defoaming agent) was prepared and transferred to a glass-lined, 500-gallon capacity kettle. The aqueous salt solution was heated to a temperature of 190° F.±5° F. The kettle was equipped with a 3-blade stirrer having a blade length of 24 inches, and revolved at approximately 75 revolutions per minute. The kettle was jacketed for steam or water to permit temperature control of the contents.

The 1250 pound batch of molten isopropyl N-phenylcarbamate was pumped from the holding tank into the stirred aqueous salt solution through a nozzle (which was a 6-inch length of ⅛-inch pipe) at a feed rate of 30 pounds per minute, while the kettle contents were cooled to 100° F.

After feeding of the isopropyl N-phenylcarbamate was completed, the suspension was stirred and was recirculated back through the kettle by pump means for 30 minutes. The kettle contents were fed to a holding tank and continuously stirred by a variable speed stirrer. From the holding tank, the slurry was fed by pump means at a rate of 2.3 to 4.0 gallons per minute to a colloid mill (ND-1 Charlottle Collvent Mill). The milled slurry was fed at a rate of from 2.3 to 4.0 gallons per minute to a C-40 continuous attritor provided with about 400 pounds of ¼ inch ceramic balls, with its agitator shaft turning at 160 rpm. The attritor effluent was collected in a product tank. The final product contained 50 percent by weight of particles of isopropyl N-phenylcarbamate (which particles were within the size range of 1 to 20 microns) dispersed in an aqueous solution of potassium chloride having a specific gravity of 1.166–1.170. A sample of the dispersion remained homogeneous when centrifuged at ambient temperature for 5 minutes at 2200 rpm at a radius of 6 inches.

While the invention has been described with reference to specific details of certain illustrative embodiments, it is not intended that it shall be limited thereby, except insofar as such details appear in the accompanying claims.

We claim:

1. A process for preparing a stable, flowable, aqueous dispersion of carbamate compound selected from isopropyl N-phenylcarbamate, isopropyl N-m-chlorophenyl carbamate, 4-chlorophenyl N-methyl carbamate, 4-chlorophenyl N,N-dimethyl carbamate or 2-chlorophenyl N-n-propyl carbamate by injecting molten carbamate into a stirred aqueous solution of inorganic alkali or alkaline earth metal salt, said salt solution having a specific gravity of from 90 to 110 percent of the specific gravity of the molten carbamate and being maintained at a temperature of from about 10° C. to about 50° C. below the temperature of the molten carbamate, the molten carbamate being injected into the salt solution at a rate such that the molten carbamate penetrates beneath the surface of the salt solution and forms therein a suspension of carbamate particles, at least 80 percent of said particles having a size in the range of 500 to 3500 microns and wet-milling and thus formed suspension to produce an aqueous carbamate dispersion containing from about 10 to about 70 weight percent carbamate wherein the size of the carbamate particles is less than 20 microns.

2. The process of claim 1 wherein the aqueous salt solution is an aqueous potassium chloride solution.

3. The process of claim 1 wherein the size of the carbamate particles in the dispersion is less than 10 microns.

* * * * *